United States Patent
Hubbard, Jr.

(10) Patent No.: US 11,571,541 B2
(45) Date of Patent: Feb. 7, 2023

(54) APPARATUS AND METHODS OF TRANSCRANIAL STIMULATION TO ADJUST SENSORY CORTICAL DENDRITIC SPINE NECK MEMBRANE POTENTIALS FOR ALTERING CONSCIOUSNESS

(71) Applicant: David Richardson Hubbard, Jr., Poway, CA (US)

(72) Inventor: David Richardson Hubbard, Jr., Poway, CA (US)

( * ) Notice: Subject to any disclaimer, the term of this patent is extended or adjusted under 35 U.S.C. 154(b) by 233 days.

(21) Appl. No.: 17/081,826

(22) Filed: Oct. 27, 2020

(65) Prior Publication Data

US 2022/0126055 A1 Apr. 28, 2022

(51) Int. Cl.
*A61M 21/00* (2006.01)
*A61N 1/36* (2006.01)
(Continued)

(52) U.S. Cl.
CPC ......... *A61M 21/00* (2013.01); *A61N 1/36025* (2013.01); *A61N 2/002* (2013.01); *A61N 2/006* (2013.01); *A61N 5/0622* (2013.01); *A61N 7/00* (2013.01); *A61B 5/0036* (2018.08); *A61B 5/0042* (2013.01); *A61B 5/0075* (2013.01); *A61B 5/055* (2013.01); *A61B 5/24* (2021.01); *A61B 5/245* (2021.01); *A61B 5/369* (2021.01); *A61B 5/389* (2021.01); *A61M 2021/0077* (2013.01); *A61M 2202/048* (2013.01); *A61N 2007/0026* (2013.01)

(58) Field of Classification Search
CPC ............ A61N 1/36034; A61N 1/36025; A61N 5/0622; A61N 7/00; A61N 2007/0026; A61N 2/006; A61N 1/36031; A61N 2/002; A61B 5/24; A61B 5/389; A61B 5/055; A61B 5/0075; A61B 5/377; A61B 5/245; A61B 5/369; A61B 5/0036; A61B 5/0042; A61M 2021/0077; A61M 2202/048; A61M 21/00
See application file for complete search history.

(56) References Cited

U.S. PATENT DOCUMENTS 4,664,117 A 5/1987 Beck
4,979,508 A 12/1990 Beck
(Continued)

FOREIGN PATENT DOCUMENTS

WO 2013173875 A1 11/2013

OTHER PUBLICATIONS

Internet Archived Deluca Massage services page from 2018. (https://web.archive.org/web/20180123175924/https://www.delucamassage.com/services/) (Year: 2018).*
(Continued)

*Primary Examiner* — Christine H Matthews
*Assistant Examiner* — Joshua Daryl D Lannu
(74) *Attorney, Agent, or Firm* — Chen-Chi Lin

(57) ABSTRACT

A method facilitates altering consciousness by transcranial stimulation to adjust the membrane potential duration of sensory cortex dendritic spine necks. Sensory cortex spine neck membranes are conscious. The method comprises the steps of placing electrodes on or near a scalp; applying electric fields to spine neck membranes in sensory cortex; adjusting stimulation parameters; and altering consciousness for a predetermined duration.

8 Claims, 4 Drawing Sheets

(51) Int. Cl.
  *A61N 2/00*   (2006.01)
  *A61N 5/06*   (2006.01)
  *A61N 7/00*   (2006.01)
  *A61B 5/00*   (2006.01)
  *A61B 5/055*  (2006.01)
  *A61B 5/24*   (2021.01)
  *A61B 5/245*  (2021.01)
  *A61B 5/369*  (2021.01)
  *A61B 5/389*  (2021.01)

(56) References Cited

U.S. PATENT DOCUMENTS

| | | |
|---|---|---|
| 5,123,899 A | 6/1992 | Gall |
| 7,621,272 B2 | 11/2009 | Or |
| 8,090,446 B2 | 1/2012 | Fowler et al. |
| 9,067,052 B2 | 6/2015 | Moses et al. |
| 9,227,056 B1 | 1/2016 | Heldman et al. |
| 10,029,113 B2 | 7/2018 | Zangen et al. |
| 10,118,038 B2 | 11/2018 | De Ridder |
| 10,335,606 B2 | 7/2019 | Pell et al. |
| 10,589,118 B2 | 3/2020 | Schneider |
| 2002/0173729 A1* | 11/2002 | Viertio-Oja ........... A61M 16/18 600/545 |
| 2005/0070971 A1 | 3/2005 | Fowler et al. |
| 2007/0288072 A1* | 12/2007 | Pascual-Leone .. A61N 1/36171 607/88 |
| 2011/0110942 A1 | 5/2011 | Kallop et al. |
| 2014/0207224 A1 | 7/2014 | Simon |
| 2014/0316217 A1 | 10/2014 | Purdon et al. |
| 2015/0174418 A1 | 6/2015 | Tyler et al. |
| 2015/0238762 A1 | 8/2015 | Pal et al. |
| 2017/0182285 A1* | 6/2017 | Tyler .................... A61B 5/4806 |
| 2019/0001133 A1 | 1/2019 | Onarheim et al. |
| 2019/0105517 A1 | 4/2019 | Tyler |
| 2019/0201707 A1 | 7/2019 | Stubbeman |
| 2019/0247654 A1 | 8/2019 | Alyagon et al. |
| 2019/0374786 A1* | 12/2019 | Jorgensen ................ A61N 2/02 |

OTHER PUBLICATIONS

Blaize et al., "Functional ultrasound imaging of deep visual cortex in awake nonhuman primates", Jun. 8, 2020, 117 (25) 14453-14463, PNAS 1916787117.

Crick et al., "Are we aware of neural activity in primary visual cortex", Nature vol. 375, pp. 121-123, 1995.

Kasteleijn-Nolst Trenite et al., "Photic stimulation: Standardization of screening method", Epilepsia, 40, Suppl. 4, 75-79, 1999.

Meader et al., "Physiology of somatosensory perception: cerebral lateralization and extinction" Neurology 51, 721-727, 1998.

* cited by examiner

APPARATUS AND METHODS OF TRANSCRANIAL STIMULATION TO ADJUST SENSORY CORTICAL DENDRITIC SPINE NECK MEMBRANE POTENTIALS FOR ALTERING CONSCIOUSNESS

BACKGROUND OF THE INVENTION

Brain Stimulation and Consciousness

Brain stimulation is performed with electrodes that are implanted into the brain, attached to the brain surface, or placed outside the skull. Stimulation is electrical or magnetic which both create electric fields in the brain, and also is ultrasonic. Brain structure targets are both cortical and subcortical. Regions of interest include amygdala, nucleus accumbens, hippocampus, cingulate, BA25, motor and sensory cortex. Also called neuronal stimulation and transcranial stimulation, brain stimulation is used to treat neurological and psychiatric diseases and to research brain function. The term is distinguished from high-voltage stimulation such as electroconvulsive, electrosleep, or cranial electrotherapy. Brain stimulation creates electric fields around neurons whereby neuronal firing rates are increased or decreased. The electric field around the neuron cell body modulates its firing rate (action potential frequency) during the stimulation and for a period of time after stimulation. Depending on the depth and radius from the stimulating electrode, different brain regions are targeted for the purpose of adjusting firing rates whereby they persist beyond the duration of stimulation. Transcranial stimulation affects the action potentials, postsynaptic potential, and the resting membrane potential. Action potentials are optimally modulated if the electric field is longitudinal to the axon's length from soma to synapse. Along the axon, the action potential duration is 1-2 milliseconds. The postsynaptic potentials arrive as waves down the dendrites to the soma where they are summated at the axon hillock section of the cell body (soma). When the membrane potential at the axon hillock reaches its threshold, an action potential is fired by rapid opening of membrane channels for positively charged calcium, sodium, and potassium ions, and negatively charged chloride ions. The action potential propagates by jumping to the nodes of Ranvier between sections of insulating myelin. Brain stimulation is thought to influence dendritic polarization, soma summation, axonal propagation and synaptic processes. It can evoke a behavioral response or not. The thresholds have been determined empirically. For example, with direct cortical stimulation at progressively longer pulse trains, the threshold for sensory perception, i.e., when the patient reports conscious perception, occurs at about 250 milliseconds; the perception threshold does not change with longer trains. Evoked potentials are observed below the sensory perception threshold. No motor responses are observed at that level of stimulation. The thresholds are the same in the visual cortex. After peripheral stimulation for 20-30 milliseconds, evoked potentials recorded from the primary somatosensory area are present whether or not the stimulus is consciously perceived. Somatosensory evoked responses are not unconscious.

Detection of direct stimulation of the brain is slower than when the stimulation is peripheral front target receptors. For example, stimulation of the sensory strip is detected more slowly than when the stimulation is coming from the peripheral receptors using haptic (grasping touch) stimuli from the fingers. Stimuli arrive in the primary sensory cortex 20 milliseconds after application to the hand. Reaction time for tactile perception is 210 to 400 milliseconds. Visual and auditory reaction time is 200 milliseconds ranging from 150 to 350 milliseconds depending on age. Visual stimulus recognition time is 53 milliseconds; movement initiation time is 80 milliseconds; detection time is 120 milliseconds. The standard movie film frame rate of 30 frames per second is 33 milliseconds.

Ultrasound, including functional ultrasound, has also been used on the cerebral cortex, as both a monitoring and stimulating method.

Intermittent photic stimulation is a component of the routine clinical EEG. A strobe light is flashed in the patient's eyes while observing the EEG for neuronal responses, typically provoked at 15-20 Hz (50-70 milliseconds). The origin of alpha, beta, theta and gamma EEG remains controversial.

Summaries of Prior Art on Brain Stimulation and Consciousness

U.S. Pat. No. 10,589,118 (Schneider, 2020) claims a method of transcranial magnetic stimulation over deep brain regions comprising one or more of thalamus, cingulate, putamen, caudate nucleus, hippocampus, ventral striatum, and amygdala, and using a plurality of electromagnets positioned to achieve spatial summation of signals—action potentials—at the deep brain region, for treating depression, addiction, or pain. The transcranial magnetic stimulation is applied to the predetermined cortical region.

U.S. Pat. Appl. Publication No. 2019/0247654 (Alyagon, 2019) claims a transcranial magnetic stimulation device for use with EEG (electroencephalography) for treating attention deficit disorder.

U.S. Pat. Appl. Publication No. 2019/0,201,707 (Stubbeman, 2019) claims a therapeutic or diagnostic device for stimulating peripheral and central nervous systems at theta frequencies, from 3 to 28 Hz.

U.S. Pat. No. 10,335,606 (Pell et al., 2019) claims a transcranial magnetic stimulation method for modulating the blood brain barrier by providing a series of magnetic pulses at frequencies ranging from 0.2 Hz to 2 Hz, and amplitudes 120-130% of the resting motor threshold amplitude for treatment of intracranial tumors and administration of pharmaceutical substances. to temporarily change permeability of the blood brain barrier for a period of at least 1, 3, and 5 minutes.

U.S. Pat. Appl. Publication No. 2019/0,105,517 (Tyler, 2019) claims an ultrasonic method for adjusting brain activity and monitoring the brain activity with any one of photoacoustic tomography, functional near-infrared spectroscopy, magnetoencephalography and electroencephalography (EEG), for thalamo-cortical oscillations. The target brain regions are one of: hippocampus, amygdala, thalamus, cerebellum, striatum, entorhinal cortex, auditory cortex, perirhinal cortex, entorhinal cortex, cerebral cortex, prefrontal cortex, auditory cortex, visual cortex, somatosensory cortex, motor cortex, locus coeruleus, hypothalamus, brainstem, cingulate cortex, olfactory region, proprioceptive region, afferent or efferent regions, or combination thereof.

U.S. Pat. No. 10,118,038 (De Ridder, 2018) claims a treatment for a neurological disorder by adjusting functional connectivity between at least two neural networks, and further claims to stimulate the reward system with a burst or clustered firing or noise stimulation, to stimulate at least one site from the list consisting of: amygdala, dorsal anterior cingulate, insula, and to stimulate a lateral habenula nucleus for dys- or anti-reward.

U.S. Pat. No. 10,029,113 (Zangen et al., 2018) claims a method for transcranial magnetic stimulation with two electromagnetic coils that induce electric field pulses at a threshold level which is high enough to produce an action potential in the brain region. Embodiments include series of pulses at different repetition rates or different durations wherein the providing current does not stimulate the brain region. In another embodiment the positions and design of the coil are configured to approximate a path of a neuronal bundle.

U.S. Pat. No. 9,227,056 (Heldman et al., 2016) claims a therapy for movement disorders providing a low dose anodal direct electrical current to stimulate an area of the subject's brain at a predetermined duty-cycle while the subject is sleeping.

U.S. Pat. No. 9,067,052 (Moses et al., 2015) claims a transcranial magnetic stimulation method of rotating electric fields for axonal excitation.

U.S. Pat. Appl. Publication 2015/0174418 (Tyler et al., 2015) claims a method of transcranial stimulation with spatiotemporal patterns to decrease peak current in order to stimulate a target brain region based on cognitive and physiological assessments and measurements. The method incorporates pulsed electrical stimulations with a phase shift between pulses from different sets of electrodes of less than 10 milliseconds.

U.S. Pat. Appl. Publication No. 2015/0238762 (Pal et al., 2015) claims a method of modifying a user's cognitive state using a neurostimulator worn on the user's head. The user selects an EEG waveform and adjusts the perceived intensity of stimulation. One claim comprises the user temporarily modifying the application of the waveform ensemble for a predefined timer period. Another claim comprises a configuration to evoke a phosphene, and another transiently decreases then increases the perceived intensity of the waveform ensemble.

U.S. Pat. Appl. Publication No. 2014/0207224 (Simon, 2014) claims a method of improving motor and/or memory function with an electrical impulse through an electrode to a target region in the motor cortex sufficient to modulate neurons and improve patient function.

U.S. Pat. No. 8,090,446 (Fowler et al., 2012) claims an electrical stimulation therapy using a plurality of electrodes sufficient for a desired purpose.

U.S. Pat. Appl. Publication No. 2005/0070971 (Fowler, 2005) claims a system for applying electrical stimulation to the cortical surface with an implantable pulse generator.

U.S. Pat. No. 4,664,117 (Beck, 1987) claims a voltage generator apparatus attached near the subject's retina to produce visual sensations called phosphenes for entertainment or to help a blind person to locate nearby objects. In a subsequent patent (U.S. Pat. No. 4,979,508, Beck, 1990) the device uses external inputs derived from music. Beck describes phosphenes as visual sensations experienced in the absence of normal visual stimulus. Such sensations may be induced by mechanical pressure on closed eyelids, by impact to the body, by various diseases or drugs, and by electrical stimulation of the nervous system. The inventor describes in detail his own and prior work. The types of phosphenes vary with pulse frequency and duty cycle. For example, at 20 Hz (50 millisecond pulse width) there is a definite progression of sensation types with increasing pulse duty cycle. At pulse ratios of 1:1 the patterns are round or flower-like. As the ratio decreases, i.e., as the pulses become narrower, the patterns change to lines, both straight and wavy. At very low values, such as 1:14, the pattern becomes radial or star-like. At other ratios there are pointillistic patterns. The sensation types bear a fixed within-subject relationship to frequency and pulse duty-cycle—the correlation was reproducible over six months, but between-subject correlations were insignificant. The inventor describes use of the method to induce phosphenes during hallucinogen administration.

International patent Publication No. WO 2013/173875 (Fitzgerald et al., 2013) claims a method of transcranial magnetic stimulation using a magnetic coil in varying stimulation parameters including coil orientation, current level, pulse frequency and/or pulse width and monitoring prefrontal cortex brain activity using near infra-red spectroscopy, EEG, EMG (electromyography), and/or fMRI (functional magnetic resonance imaging).

Neuronal Correlates of Consciousness

The brainstem (the top part of the spinal cord) is responsible for loss of consciousness when compressed by swelling or when twisted by a knock-out punch to the jaw. The brainstem pathways and physiology are known including those of sleep and dreaming. Dreams are sometimes conscious events. The brainstem causes loss of consciousness by inhibiting the pathways to and from the cortex. Brainstem activity is not conscious. Thus there is consensus that consciousness arises in sensory cortex. On the other hand, cortex and subcortex abnormalities do not cause generalized loss of consciousness, but instead localized losses of conscious sensations. A stroke in the sensory cortex causes discrete losses of (conscious) vision, hearing, touch and language comprehension in contrast to the global loss with brainstem dysfunction. Cortical blindness and parietal neglect are examples of unusual cortical strokes. After a parietal stroke for example a patient may not be conscious of a visual object shown on one side of the body but is nevertheless able to demonstrate use of the object. The neurologist tests for neglect by stimulating both sides of the body simultaneously and observing if the patient notices both sensations. Loss of awareness of one side or a region is called neglect or extinction and is tested in the laboratory with a procedure called masking. In a masking experiment, electric pulses are applied to both finger tips with a brief interval between. When the masking stimulus is presented shortly after the target stimulus the subject is not conscious of it. This backward mask at 50-100 milliseconds is more effective in blocking awareness of the target than masking presented at the same time as or before the target stimulus. Masking stimuli following the target by 500 to 750 milliseconds oppositely affects signal detection, enhancing perception. It has been proposed that extinction is mediated by inhibition of midbrain-thalamic-cortical neural assemblies, is modulated by gamma EEG activity that begins 85-100 milliseconds post-stimulus, and is required for (conscious) perception. There is delay in time before a stimulus becomes conscious. The controversies about whether activity in the primary sensory cortex is directly accessible to (conscious) perception persist. A direct role of thalamocortical interactions in the neural mechanisms of conscious awareness has been postulated including a role for the intralaminar nuclei of the thalamus. Current theory proposes that stimuli undergo initial subconscious processing in the primary somatosensory area and thalamo-cortical circuits or networks, before reaching consciousness somewhere in the cortex.

Nobel Prize winner Francis Crick, after discovering with James Watson the structure of DNA and the mechanism of cell reproduction, moved to California to study consciousness. As he describes in The Astonishing Hypothesis, his search for "the neuronal correlates of consciousness" (NCC) began with the prime thesis of cognitive neuroscience: neuronal firing rates are necessary and sufficient for brain functions including consciousness. The brain's firing rates and rhythms are the target of research on brain function and therapies for cognitive and psychological disorders. The analysis of focal activation/deactivation of, and functional (synchronous) connectivity between, collections of neurons is based on monitoring directly or indirectly, variations in firing rates. Based on firing rates, concepts of coding, computing, signalling, and processing are used to model brain function. Crick believed that (conscious) visual features such as facial features are "coarse coded" from firing patterns. He pointed out that a single action potential cannot single-handedly activate even one of its own postsynaptic target neurons. If every visual feature had its own 'grandmother" neuron, there would not be enough neurons in the whole cortex. Crick tentatively proposed that consciousness is created when the prefrontal cortex is stimulated by the visual cortex V4 region, up-stream from V1. Crick concluded that the neuronal correlates of consciousness remained unknown.

Prior Art on Neuronal Correlates of Consciousness

U.S. Pat. No. 5,123,899 (Gall, 1992) claims a method for altering the state of consciousness using EEG brain waves. Systems are described to stimulate specific brain wave rhythms for inducing a range of altered consciousness including heightened awareness, a hypnotic state, sleep, learning, researching, inventing, and concentrating. The patent emphasizes the utility of consciousness in work and daily life.

Anesthesia and Consciousness

General anesthesia is the gold standard for altering and losing consciousness globally. It is also dangerous. How general anesthetics cause unconsciousness is unknown. It is not mediated by the brainstem which would be a bottom-up mechanism. Current theory is that unconsciousness is caused by a reduction in the neuronal signaling from higher-order brain regions to lower order brain regions. Consciousness according to current theory, is suppressed when the anesthetic disrupts cortical to cortical, top-down, processing. One proposal places the proposed top-down effect on the dendrites that are suppressed by inhibitory neurotransmitters. Attention has focused on the neurotransmitter receptors' synthesis and density on postsynaptic neurons; a leading pharmaceutical strategy targets the NMDA receptor on the postsynaptic membrane, the NMDA spikes, spikes at the main bifurcations of apical dendrites, and dendritic calcium channels. Bottom-up axons from the thalamus terminate predominantly in cortical layer 4. Axons running in the Layer 1 canopy provide top-down connectivity from frontal to parietal, temporal, and occipital cortices, as well as top-down connectivity with the lower Layers. According to these theories, anesthesia-induced unconsciousness is caused by suppressing top-down signals at the level of the apical dendrites of pyramidal neurons in the sensory cortices, and disrupting working memory perceptual predictions.

Summary of Prior Art on Anesthesia and Consciousness

U.S. Pat. Appl. Publication No. 2014/0316217 (Purdon, 2014) claims a system and method for monitoring loss of consciousness and recovery using low frequency physiological sensors while administering a chemical such as Propofol, Etomidate, Barbiturates, Thiopental, Phenobarbital, Methohexital, Benzodiazepines, Midazolam, Diazepam, Lorazepam, Dexmedetomidine, Ketamine, Sevoflurane, Isoflurane, Desflurane, Remifenanil, Fentanyl, Sufentanil, and Alfentanil.

U.S. Pat. No. 7,621,272 (Orr, 2009) claims a method for facilitating emergence of a subject from inhaled anesthetic. Emergence is an anesthesia term for the return to wakefulness from the effects of the pharmacologic agent that rendered the patient unconscious. Altered consciousness, loss of consciousness, recovery from loss of consciousness refer to the same phenomena and brain function. Once the anesthetic concentration in the brain reaches a sufficient level, the threshold level, which depends upon a variety of subject-specific factors, including the size and weight of the subject, the subject becomes anesthetized. The subject remains anesthetized so long as the concentration of the anesthetic agent in the brain of the subject remains above the threshold level. Once the surgery is completed, it is usually desired to reverse the effects of the general anesthetic as soon as possible for better cognitive function for elderly patients immediately following surgery and enabling patients to protect their airway sooner.

Sensory Cortex Dendritic Spines and Consciousness

There are 300 trillion synapses in the cortex, divided amongst motor and sensory cortex, and amongst the six cortical layers. Several trillions are primary sensory cortex neurons. In the sensory cortex the primary sensory neuron is the pyramidal neuron, see FIG. 1. This neuron is the first cortical neuron to receive direct excitatory sensory stimuli, via the thalamus, from sensory receptors responding to the surrounding environment in the present moment. The first synapse for visual receptors in the eye is the lateral geniculate nucleus of the thalamus. The LGN has 21,000 neurons that terminate in the primary visual cortex (V1, BA17). In addition, the pulvinar nucleus of the thalamus has 31,000 neurons that terminate in the rest of the visual cortex, V2, V3, V4, and in the parietal lobe. External receptors for the other senses also terminate in the thalamus. Thalamic second-order relaying axons terminate on the sensory cortex dendritic spine postsynaptic membrane of pyramidal neurons in their respective sensory cortical regions.

Pyramidal neurons are surrounded by a fan-like spread of dendrites, including characteristic apical dendrites that travels from the cell bodies in Layer IV to Layer I where cortex-to-cortex two-way action potential signals connect the entire cortex and are presumed to engage in top-down computational processes.

The dendrites of the pyramidal neuron are studded with spines, protrusions along the dendrite membrane like thorns along a branch. Said neurons have thousands of dendrites and dendrites have thousands of spines. The head or tip of the spine is the location of the postsynaptic side of the synapse, containing the neurotransmitter receptors, including NMDA receptors. N-Methyl-D-aspartate (NMDA) is an amino acid derivative that acts as a specific agonist at the NMDA receptor mimicking the action of glutamate, the neurotransmitter which normally acts at that receptor. The number of NMDA receptors and actin skeleton molecules in the spine are increased with memory and long term potentiation. The spine neck extends outwards to the spine head from the dendritic membrane. Said spine neck diameter and length are modified by synaptic activity.

Summary of Prior Art on Sensory Cortex Dendritic Spines and Consciousness

U.S. Pat. Appl. Publication No. 2011/0110942 (Kallop et al., 2011) claims a method of increasing the number of dendritic spines along dendrites (density) by injecting an immunological receptor protein into spinal fluid in the cerebral ventricles in mice. DR6 is a membrane receptor protein found especially in immune cells and dendrites. The patent proposes to treat patients with cognitive or psychiatric disorders and for enhancing cognition.

Excitatory neurotransmitters, secreted from the presynaptic axon bouton, bind to postsynaptic receptors on the spine head, causing the spine membrane to open channels for electrically charged sodium, potassium, calcium and chloride ions. The change in membrane potential spreads outwards from the postsynaptic spine head, through the spine neck into the dendrite main channel, where local membrane potentials are amplified along the dendritic membrane including at bifurcations of dendrite branches; these membrane changes are referred to as dendritic summation, dendritic signaling, and apical dendrite amplification. The excitatory postsynaptic potential, EPSP, is longer in the neck than in the dendrite, soma, or axon. The spine neck's length and diameter create electrical resistance relative to surrounding membrane regions of the neuron. Electric resistance in the spine neck prolongs the membrane potential. Longer and narrower spine necks produce EPSPs of longer duration. EPSPs are prolonged by capacitive discharge during their falling phase. EPSP standardization relies on spine morphology and the associated spine neck resistance that links synapses on spine heads with dendrites, independent of location on neurons' antenna-like dendrites. Spine neck resistance amplifies membrane depolarization up to 45-fold. The neuronal membrane time constant is shorter in somatosensory pyramidal cells than prefrontal pyramidal cells. It has been proposed that EPSPs in dendritic spines may standardize local EPSP properties throughout the dendritic tree, thereby allowing neurons to use similar voltage-sensitive postsynaptic mechanisms at all dendritic locations.

SUMMARY OF THE INVENTION

No Prior Art on Spine Potentials and Consciousness. A method facilitates altering consciousness by transcranial stimulation to adjust a membrane potential duration of sensory cortex dendritic spine necks. The method comprises the steps of placing electrodes on or near a scalp; applying electric fields to spine neck membranes in sensory cortex; adjusting stimulation parameters; and altering consciousness for a predetermined duration.

DETAILED DESCRIPTION OF FIGURES AND EMBODIMENTS

Figure 1:
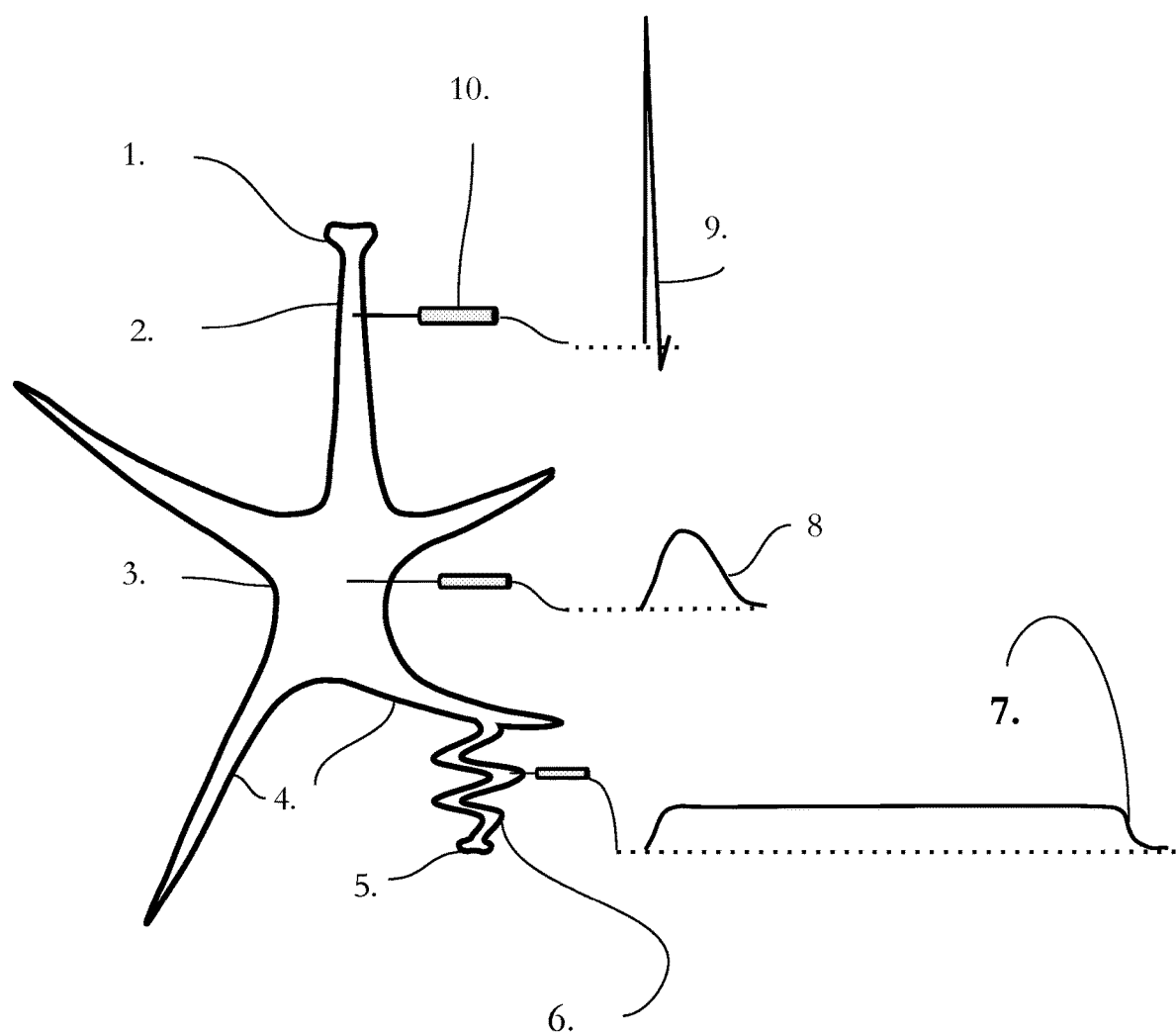
FIG. 1 is a primary sensory cortex neuron, emphasizing the dendritic spine neck, one of trillions in the sensory cortex.

FIG. 1 is a sensory cortex neuron emphasizing the dendritic spine neck.

Ref. 1. The presynaptic axon bouton. Here the neuron stores and releases neurotransmitters to excite or inhibit recipient neurons (not drawn). The synapse is the basis of neuronal chemical communication.

Ref. 2. The axon. The axon transmits the neuron membrane potential to the synapse (1). The membrane potential during an action potential is 1-2 milliseconds (9). Propagation speed is increased by myelin insulation. Analysis of the firing rate of action potentials is the basis of cognitive neuroscience.

Ref. 3. The cell body—the soma. The changing membrane potentials along the cell summate here to reach the threshold that fires the action potential. These neurons are the first-line cortical receivers of sensory input from the sensory receptors: the eye, ear, skin, mouth, and inside the body that are relayed to the cortex from the thalamus.

Ref. 4. The dendrites. labels two of the four dendrites protruding from the soma. The dendrites contain the receptors for sensory inputs from the thalamic sending neuron and pass them along the membrane to the soma.

Ref. 5. The spine head. In sensory cortex pyramidal neurons, the dendritic receptors along the dendrite are located on top of characteristic bumps along their membrane surface called spines where the receptors are densely clustered at the postsynaptic side of the synapse. The postsynaptic membrane is embedded with receptors in particular NMDA receptors that change with long-term potentiation and memory.

Ref. 6. The spine neck. The shape and size of the spine neck relative to the neuron is drawn to emphasize the unique and hitherto unexplained electrical resistance levels. The spine neck contains a skeleton of actin molecules that determines its diameter and length, its capacitance and resistance. The shape and resistance vary over time and with synaptic activity. There are 300 trillion synapses in the brain. Spine neck duration and location are not determined by the pyramidal neuron it is protruding from.

Ref. 7. The spine neck membrane potential. Sensory cortex spine neck membrane potentials sufficient duration are conscious.

Ref 8. An excitatory postsynaptic potential (EPSP). The electrode piercing the soma is registering an EPSP after synaptic activation. The amplitude and duration is compared to that of the spine neck in Ref. 7. The duration of soma and dendrite membrane potential changes are below the threshold for conscious sensation.

Ref. 9. An action potential. A membrane action potential is a 1-2 millisecond spike that travels down the axon to the synapse to cause the release of neurotransmitters. Firing rates of action potentials vary over time and in different neuronal groups. The firing rates are analyzed to create representative models of brain function including consciousness although action potentials are below the duration threshold for conscious detection.

Ref 10. A dendrite spine electrode. The electrode apparati are described in FIGS. 3 and 4.

Figure 2:
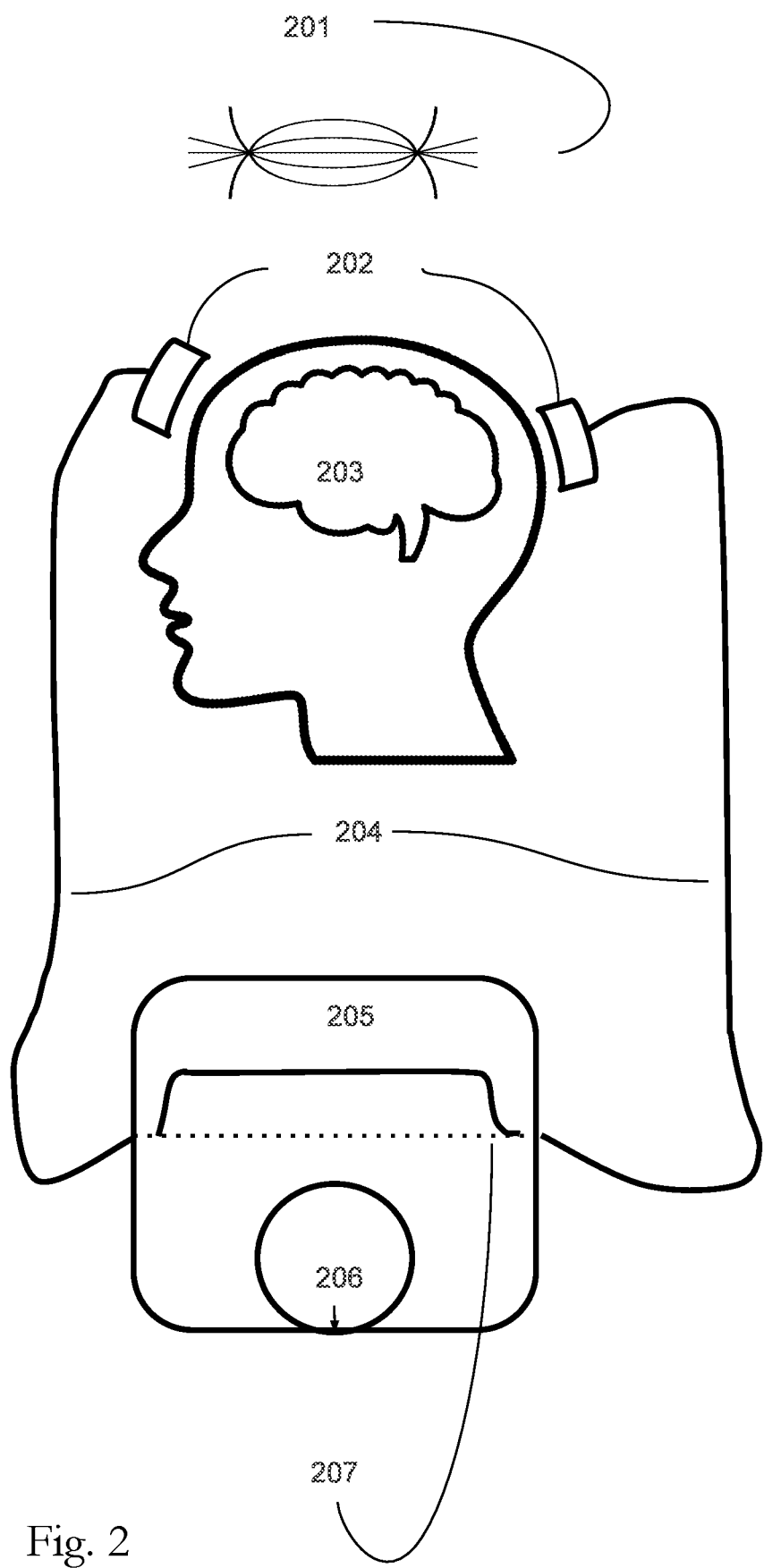
FIG. 2 is a user altering consciousness by stimulating dendritic spine-neck membrane potentials.

FIG. 2 is a user altering consciousness by stimulating dendritic spine-neck membrane potentials.

The stimulating field, Ref 201, is adjusting the duration of the membrane potential of sensory cortical dendritic spine necks, referenced in FIG. 1, Ref 7. Said membrane potentials are adjusted by any one of electrical, magnetic, transcranial, direct, anodal, cathodal, alternating, rotating, intermittent photic (visual), a plurality of external sensory receptors, including but not limited to auditory, and somatosensory, ultrasound, functional ultrasound, chemical, anesthetic agent, a combination thereof. In one embodiment a transcranial device, Ref. 202, is placed on or near the user's head, Ref 203 and connected by wires, Ref 204, to a control device, Ref 205, that is user-adjusted, Ref 206. The stimulation parameters include but are not limited to pulse width, pulse rise time, pulse fall time, interval, amplitude, orientation, duty-cycle and frequency. The locations of the stimulating electrodes are adjusted to position the fields on the membrane potentials. These parameters are optimized to alter the membrane potentials in a selected cortical region that includes primary sensory cortical neurons including their dendrites. The sensations reported by the user are used to modulate the perceived intensity. Brain regions include but are not limited to, occipital, parietal, temporal, insular cortices, and primary sensory receptors in the frontal cortex, brainstem and spinal cord. In one embodiment the spine neck membrane durations in cortical regions are monitored with any of near infra-red spectroscopy, ultrasound, functional ultrasound, magnetoencephalography, EEG, EMG, fMRI, dendrite spine electrodes, a combination thereof, with user feedback on monitored activity including but not limited to cortical location and duration of said potentials.

Figure 3:
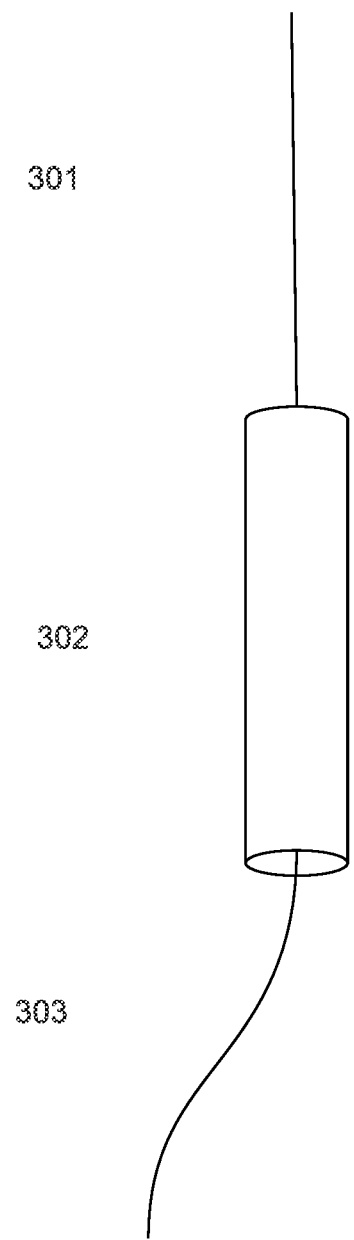
FIG. 3 is a dendritic spine electrode.
Figure 4:
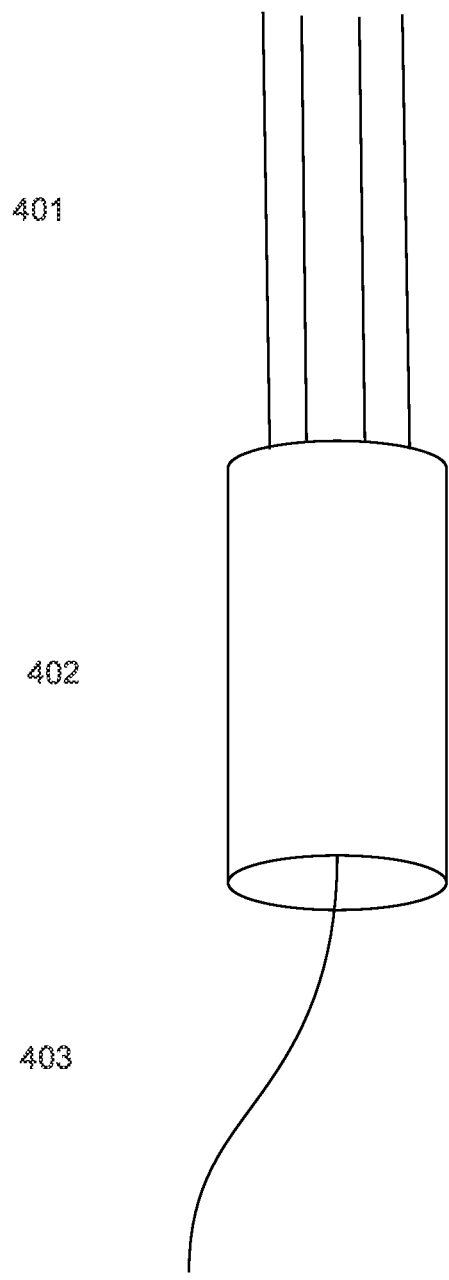
FIG. 4 is an apparatus for a plurality of dendritic spine electrodes

FIG. 3 is a dendrite electrode. The drawing shows a needle electrode and its attachment to a wire. In one embodiment, Ref 301 is a needle electrode, Ref 302 is an apparatus to hold and connect the electrode to a wire, Ref. 303. FIG. 4 is an apparatus for a plurality of dendrite electrodes. FIG. 4 shows one embodiment of an apparatus for a plurality of electrodes. Ref. 401 shows a plurality of needle electrodes; Ref 402 holds and connects the electrodes to a wire, Ref 403. This embodiment records simultaneously from any of axon action potentials, soma summation, postsynaptic EPSPs, spine neck membrane, a combination thereof over sufficient time intervals to study conscious sensory detection thresholds and receptive fields. In one embodiment the spine neck membrane durations in cortical regions are monitored with any of near infra-red spectroscopy, ultrasound, functional ultrasound, magnetoencephalography, EEG, EMG, fMRI, a combination thereof, with user feedback on monitored activity including but not limited to cortical location and duration of said potentials.

I claim:

1. A method of adjusting a membrane potential duration of sensory dendritic spine necks for altering consciousness, the method comprising the steps of
    applying stimulation to a plurality of neurons; and
    adjusting stimulation parameters;
    wherein the method further comprises altering the consciousness for a predetermined duration;
    wherein the step of applying the stimulation to the plurality of neurons comprises placing electrodes on or near a scalp; and
        applying electric fields to spine neck membranes in sensory cortex; and
    wherein the stimulation parameters comprise location, direction, frequency, amplitude and duty cycle.

2. The method of claim 1 further comprising monitoring membrane potentials at neuron locations consisting of axon, soma, dendrite, synapse, and spine neck, using near infra-red spectroscopy, ultrasound, functional ultrasound, magnetoencephalography, EEG, EMG, fMRI, dendrite spine electrodes, or a combination thereof; and receiving user feedback on monitored activity comprising cortical location and the membrane potential duration.

3. A method for altering consciousness of a user, the method comprising the steps of applying stimulation to a plurality of neurons;
    receiving feedback from the user;
    adjusting parameters of the stimulation; and
    altering the consciousness of the user for a predetermined duration;
    wherein the parameters of the stimulation comprise changing a direction; and
    wherein the stimulation is from a plurality of peripheral receptors positioned at different directions;
    wherein the parameters of the stimulation further comprise changing a duty cycle.

4. The method of claim 3 further comprising placing electrodes on or near a scalp; and applying electric fields to spine neck membranes in sensory cortex.

5. A method of adjusting a membrane potential duration of sensory dendritic spine necks for altering consciousness, the method comprising the steps of placing electrodes on or near a scalp;
    applying electric fields to spine neck membranes in sensory cortex; and
    adjusting stimulation parameters of the application of the electric fields;
    wherein the stimulation parameters comprise location, direction, frequency, amplitude and duty cycle; and
    wherein the method further comprises altering the consciousness for a predetermined duration.

6. The method of claim 5 further comprising monitoring membrane potentials at neuron locations consisting of axon, soma, dendrite, synapse, and spine neck, using near infra-red spectroscopy, ultrasound, functional ultrasound, magnetoencephalography, EEG, EMG, fMRI, dendrite spine electrodes, or a combination thereof; and receiving user feedback on monitored activity comprising cortical location and the membrane potential duration.

7. The method of claim 5 further comprising applying chemical stimulation.

8. The method of claim 5 further comprising applying anesthetic agent stimulation.

* * * * *